United States Patent [19]

Ueno et al.

[11] Patent Number: 5,096,927
[45] Date of Patent: Mar. 17, 1992

[54] TREATMENT OF HEPATOBILIARY DISEASE WITH 15-KETO-PROSTAGLANDIN COMPOUNDS

[75] Inventors: Ryuji Ueno; Hiroyoshi Osama, both of Hyogo, Japan

[73] Assignee: K.K. Ueno Seiyaku Oyo Kenkyujo, Osaka, Japan

[21] Appl. No.: 600,048

[22] Filed: Oct. 19, 1990

[30] Foreign Application Priority Data

Oct. 20, 1989 [JP] Japan .................................... 274606

[51] Int. Cl.$^5$ .................. A61K 31/19; A61K 31/215; A61K 31/557
[52] U.S. Cl. .................................... 514/530; 514/573
[58] Field of Search ................................ 514/573, 530

[56] References Cited

U.S. PATENT DOCUMENTS

| | | | |
|---|---|---|---|
| 4,374,856 | 2/1983 | Ruwart | 514/412 |
| 4,464,388 | 8/1984 | Sakai | 514/412 |
| 4,503,058 | 3/1985 | Sakai | 514/412 |

FOREIGN PATENT DOCUMENTS

| | | |
|---|---|---|
| 153858 | 2/1985 | European Pat. Off. . |
| 0345951 | 5/1987 | European Pat. Off. . |
| 0281239 | 1/1988 | European Pat. Off. . |
| 0330511 | 2/1988 | European Pat. Off. . |
| 0284180 | 4/1988 | European Pat. Off. . |
| 0289349 | 5/1988 | European Pat. Off. . |
| 0292177 | 9/1988 | European Pat. Off. . |
| 0308135 | 9/1988 | European Pat. Off. . |
| 0310305 | 9/1988 | European Pat. Off. . |
| 0342003 | 5/1989 | European Pat. Off. . |
| 03439045 | 5/1989 | European Pat. Off. . |

OTHER PUBLICATIONS

JPA-129218/1987 and Chem. Abst., 107, 223291z.
Aeta Physiologica Scandinavica, 66, pp. 509-510 (1966).

Primary Examiner—Stanley J. Friedman
Attorney, Agent, or Firm—Sughrue, Mion, Zinn Macpeak & Seas

[57] ABSTRACT

A method for treatment of a hepatobiliary disease which comprises administering, to a subject in need of such treatment, a 15-ketoprostaglandin compound in an amount effective in treatment of the hepatobiliary disease.

15 Claims, No Drawings

TREATMENT OF HEPATOBILIARY DISEASE WITH 15-KETO-PROSTAGLANDIN COMPOUNDS

BACKGROUND OF THE INVENTION

Field of the Invention

The present invention relates to a method for treatment of a hepatobiliary disease which comprises administering a 15-ketoprostaglandin compound to a subject. Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

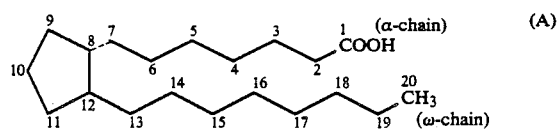

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

| Subscript 1 | 13,14-unsaturated-15-OH |
| Subscript 2 | 5,6- and 13,14-diunsaturated-15-OH |
| Subscript 3 | 5,6- 13,14- and 17,18-triunsaturated-15-OH |

Further, PGFs are sub-classified according to the configuration of hydroxy group at 9 into α(hydroxy group being in the alpha configuration) and β(hydroxy group being in the beta configuration).

BACKGROUND INFORMATION $PGE_1$, $PGE_2$ and $PGE_3$ are known to have vasodilating, hypotensive, gastro-juice reducing, intestine-hyperkinetic, uterine contracting, diuretic, bronchodilating and anti-ulcer activities. Also, $PGF_{1\alpha}$, $PGF_{2\alpha}$ and $PGF_{3\alpha}$ are known to have hypertensive, vasocontracting, intestine-hyperkinetic, uterine contracting, luteo-regressive and bronchocontracting activities.

U.S. Pat. No. 4,374,856 discloses the hepatocyte-protecting action of 15-methyl-$PGE_2$ and 16,16-dimethyl-$PGE_2$ JP-A-164512/1983 discloses the cell (including hepatocyte)-protecting action of 15-cycloalkyl-6-oxo-$PGE_1$, 15-cycloalkyl-$PGI_1$ and $I_2$, 15-cycloalkyl-6,9α-nitrilo-$PGFI_1$ and 15-cycloalkyl-6,9α-thio-$PGI_1$ and $I_2$. JP-A-203911/1983 discloses the cell (including hepatocyte)-protecting action of certain 6-oxo-$PGE_1$ and $PGI_2$ having methyl group(s) at one or two of positions 15, 16, 17 and 20 and specific 15-cyclopentyl-$PGI_1$. JP-A-129218/1987 discloses that 4- or 7-thia-$PGE_1$ may be used for treating hepatopathy. All these compounds, however, do not belong to 15-keto-PGs or their derivatives.

European Patent Application No. 0,310,305 describes that 15-keto-PGs can be used as catharitics.

In addition, some 15-keto (i.e. having an oxo group at position 15 in place of the hydroxy group) prostaglandins and 13,14-dihydro-15-ketoprostaglandins are known as substances naturally produced by enzymatic actions during metabolism of primary PGs (Acta Physiologica Scandinavica, 66, 509, 1966). It has also been described that 15-ketoprostaglandin $F_{2\alpha}$ has an anti-pregnant activity. However, it has not been reported that 15-ketoprostaglandin compounds are therapeutically effective in the treatment of a hepatobiliary disease.

As a result of extensive studies about the biological properties of 15-ketoprostaglandin compounds, the present inventors have discovered that these compounds have an activity of treating a hepatobiliary disease.

SUMMARY OF THE INVENTION

In a first aspect, the present invention provides a method for treatment of a hepatobiliary disease which comprises administering, to a subject in need of such treatment, a 15-ketoprostaglandin compound in an amount effective in treatment of the hepatobiliary disease.

In a second aspect, the present invention provides a use of a 15-ketoprostaglandin compound for the manufacture of a medicament for treatment of a hepatobiliary disease.

In a third aspect, the present invention provides a pharmaceutical composition for treatment of a hepatobiliary disease comprising a 15-ketoprostaglandin compound in association with a pharmaceutically acceptable carrier, diluent or excipient.

DETAILED DESCRIPTION OF THE INVENTION

As used herein, the term "hepatobiliary disease" means all conditions having etiology based on or accompanied by disorder of hepatocyte and conditions having etiology based on or accompanied by disorder of biliary tract, and includes hepatopathy, fulminant hepatitis, fatty liver (especially alcoholic), hepatic coma, various acute or chronic hepatitis (e.g. alcoholic, toxic, type A-viral, type B-viral, non-A non-B type-viral, serum, chronic active, etc.), hepatolenticular degeneration, hepatic hypertrophy, portal hypertension, obstructive jaundice, liver abscess, cirhosis (especially alcoholic or biliary), parasitic hepatopathy, hepatophyma, liver tuberculosis, choloecystisis, cholelithiasis, cholangitis, biliary colic, fat hypersensitivity etc.

As used herein, the term "treatment" or "treating" refers to any means of control of a disease in a mammal, including preventing the disease, curing the disease, relieving the disease and arresting or relieving the development of the disease.

The term "15-ketoprostaglandin compounds", referred to as 15-keto-PG compounds, include any prostaglandin derivatives which have an oxo group in place of the hydroxy group at position 15 of the prostanoic acid nucleus irrespective of the presence or absence of the double bond between positions 13 and 14.

Nomenclature

Nomenclature of 15-keto-PG compounds herein uses the numbering system of prostanoic acid represented in formula (A) shown above.

While formula (A) shows a basic skeleton having twenty carbon atoms, the 15-keto-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-keto-PG compounds having 10 carbon atoms in the ω-chain is nominated as 15-keto-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-keto-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-keto-PG compounds is based upon the prostanoic acid. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-4-fluoro-3-oxo-1-octyl]-5-oxocyclopentyl}-hept-5-enic acid. 13,14-dihydro-15-keto-20-ethyl-11-dehydroxy-11R-methyl-PGE$_2$ methyl ester is methyl 7-{(1R,2S,3S)-3-methyl-2-[3-oxo-1-decyl]-5-oxo-cyclopentyl}-hept-5-enoate. 13,14-dihydro-6,15-diketo-19-methyl-PGE$_2$ ethyl ester is ethyl 7-{(1R,2S,3S)-3-hydroxy-2-(7-methyl-3-oxo-1-octyl)-5-oxo-cyclopentyl}-6-oxo-heptanoate. 13,14-dihydro-15-keto-20-ethyl-PGF$_{2\alpha}$ isopropyl ester is isopropyl (Z)-7-[(1R,2R,3R,5S)-3,5-dihydroxy-2-{3-oxo-1-decyl}-cyclopentyl]-hept-5-enoate. 13,14-dihydro-15-keto-20-methyl-PGF$_{2\alpha}$ methyl ester is methyl (Z)-7-[(1R,2R,3R,5S)-3,5-dihydroxy-2-{3-oxo-1-nonyl}-cyclopentyl]-hept-5-enonate.

Preferred Compounds

The 15-keto-PG compounds used in the present invention may be any derivatives of PG insofar as they have an oxo group at position 15 in place of the hydroxy group, and may have a double bond between positions 13 and 14 (15-keto-PG subscript 1 compounds), two double bonds between positions 13 and 14 as well as positions 5 and 6 (15-keto-PG subscript 2 compounds), or three double bonds between positions 13 and 14, positions 5 and 6 as well as positions 17 and 18 (15-keto-PG subscript 3 compounds), and may have a single bond between positions 13 and 14 (13,14-dihydro-15-keto-PG compounds).

Typical examples of the compounds used in the present invention are 15-keto-PGA, 15-keto-PGD, 15-keto-PGE, 15-keto-PGF, 13,14-dihydro-15-keto-PGA, 13,14-dihydro-15-keto-PGD, 13,14-dihydro-15-keto-PGE, and 13,14-dihydro-15-keto-PGF, wherein PG is as defined above as well as their derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 6, 16, 17, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 17 and/or 19 include lower alkyl, for example, $C_{1-4}$ alkyl, especially methyl and ethyl. Substituents on the carbon atom at position 16 include lower alkyl e.g. methyl, ethyl etc., hydroxy and halogen atom e.g. chlorine, fluorine, aryloxy e.g. trifluoromethylphenoxy, etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 16, those having a halogen atom e.g. chloro, fluoro etc. at position 17, those having a lower alkyl e.g. methyl, ethyl etc. at position 19, those having an oxo group at position 6, those having a lower alkyl, e.g. methyl, ethyl, etc. at position 20 and those having phenyl or phenoxy which are optionally substituted with halogen or haloalkyl at position 16 in place of the rest of the alkyl chain.

A group of preferred compounds used in the present invention has the formula

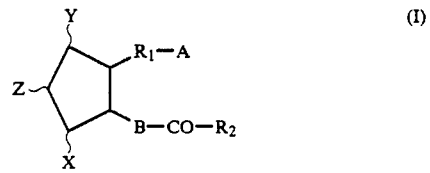 (I)

wherein
X and Y are hydrogen, hydroxy, halo, lower alkyl, hydroxy(lower)alkyl, or oxo, with the proviso that at least one of X and Y is a group other than hydrogne, and 5-membered ring may have at least one double bond, Z is hydrogen or halo, A is —CH$_2$OH, —COCH$_2$OH, —COOH or its functional derivative, B is —CH$_2$—CH=CH— or —C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for $R_1$ and $R_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 2 to 10 carbon atoms for $R_2$.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tosyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxyphenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfonylamide, ethylsulfonylamide, tolylsulfonylamide etc.

Preferred examples of A include —COOH, —COOCH$_3$, —COOCH$_2$—CH$_3$, —COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-keto-PGs, 13,14-dihydro-15-keto-PGs and their e.g. 6-keto-derivatives, $\Delta^2$-derivatives 3R,S-methyl-derivatives, 16R,S-methyl-derivatives, 16,16-dimethyl-derivatives, 16R,S-fluoro-derivatives, 16,16-difluoro-derivatives, 17S-methyl-derivatives, 20-methyl-derivatives, 20-ethyl-derivatives, 19-desmethyl-derivatives and 16-desbutyl-16-phenoxy derivatives.

When 15-keto-PG compounds of the present invention have a saturated bond between positions 13 and 14, these compounds may be in the keto-hemiacetal equilibrium by forming a hemiacetal between hydroxy group at position 11 and ketone at position 15.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese Patent Publications (unexamined) No. A-52753/1989, A-104040/1989, A-151519/1989.

Alternatively, these compounds may be prepared by a process analogous to that described herein or to known processes.

A practical preparation of the 15-keto compounds involves the following steps; referring to the Synthetic Charts I to III, reaction of the aldehyde (2) prepared by the Collins oxidation of commercially available (-)-Corey lactone (1) with dimethyl (2-oxoheptyl)phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein the ω-chain is a 13,14-dihydro-15-keto-alkyl group is prepared.

Using the above tetrahyiropyranyl ether (7), 6-keto-PGE$_1$s (15) of which a group constituted with carbon atoms at positions 5, 6 and 7 is —$_5$CH$_2$$_6$—C(O)-$_7$—CH$_2$—, may be prepared in the following steps; reduction of the tetrahyiropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at position 9 with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms at positions 5, 6 and 7 is —$_7$CH$_2$—$_6$CH=$_5$CH— may be prepared in the following steps; as shown in the Synthetic Chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above tetrahydrpyranyl ether (7) as the starting material, the compound having —$_7$CH$_2$—$_6$CH$_2$—$_5$CH$_2$— may be prepared by using the same process as that for preparing PGE$_2$ having —CH$_2$CH=CH— and subjecting the resultant compound (18) to catalytic reduction to reduce the double bond between the positions 5 and 6 followed by removal of the protective groups.

Synthesis of 5,6-dehydro-PGE$_2$s having —$_7$CH$_2$—$_6$C≡C$_5$— may be carried out by capturing a copper enolate formed by 1,4-addition of a monoalkylcopper complex or a dialkylcopper complex of the following formulae:

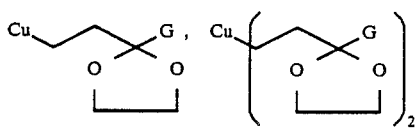

wherein G is alkyl, to 4R-t-butyldimethylsilyloxy-2-cyclopenten-1-one with 6-alkoxycarbonyl-1-iodo-2-hexyne or the derivatives.

The 11-β type PGEs can be prepared according to the Synthetic Chart III.

PGE derivatives having a methyl group at position 11 in place of hydroxy can be prepared by reacting a dimethyl copper complex with PGA-type compound obtained by subjecting 9-hydroxy-11-tosylate to the Jones oxidation. Alternatively, they can be prepared by protecting the carbonyl of saturated ketone (4) produced by reducing unsaturated ketone (3), eliminating p-phenylbenzoyl and tosylating the produced alcohol, treating with DBU to form a lactol, introducing the alpha-chain by Wittig reaction, oxidizing the alcohol at position 9 to give PGA-type compound, and reacting the product with dimethyl copper complex in order to introduce a methyl group into position 11 to give an 11-methyl-PGE-type compound, which on reduction with e.g. sodium borohydride gives an 11-methyl-PGF-type compound. An 11-hydroxymethyl-PGE-type compound, is obtained by a benzophenone-sensitized photoaddition of methanol of PGA-type compound, which is reduced with, e.g. sodium borohydride, to give an 11-hydroxymethyl-PGF-type compound. The 16-mono- or 16,16-di-halo type PGEs can be prepared according to the synthetic chart IV. The synthetic route for the compounds used in the present invention is not limited to the that described above one and may vary using different protecting, reducing and/or oxidizating methods.

Corresponding other PG compounds can be produced analogously.

Synthetic Chart I

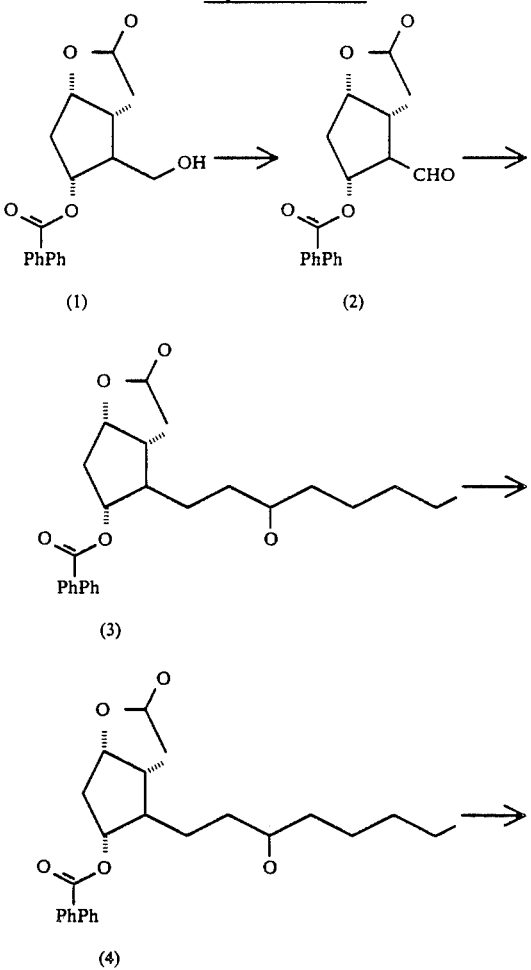

-continued
Synthetic Chart I
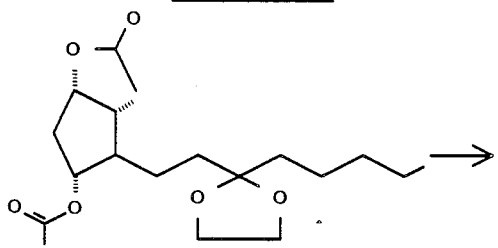
(5)
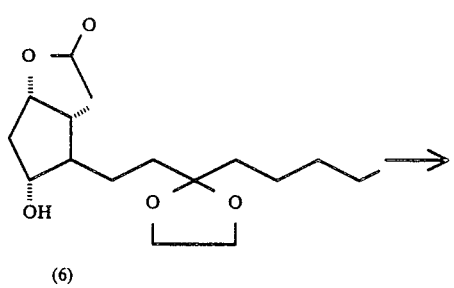
(6)
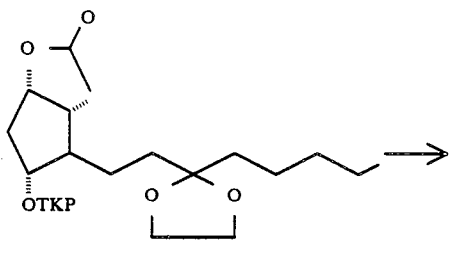
(7)
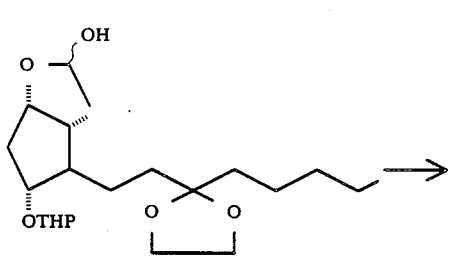
(8)
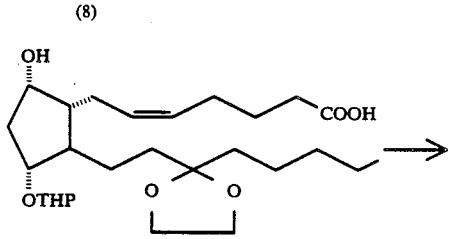
(9)
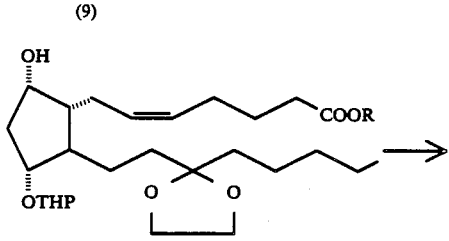
(10)
-continued
Synthetic Chart I
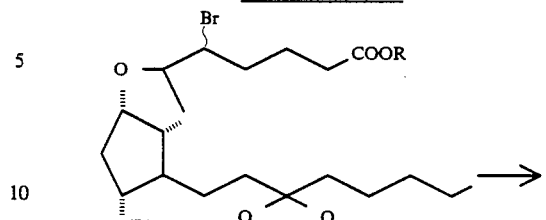
(11)
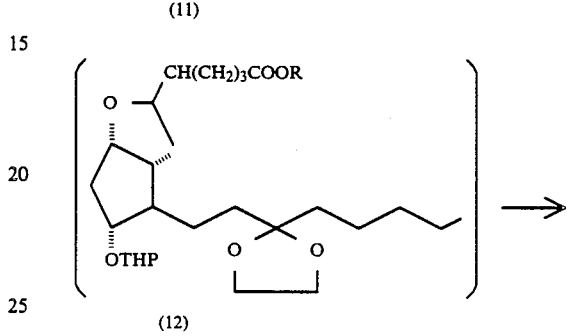
(12)
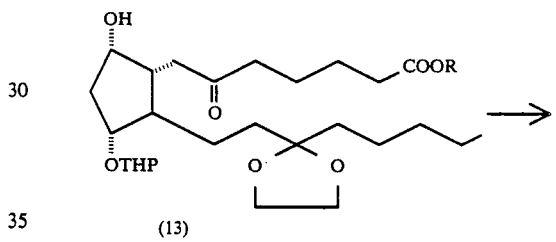
(13)
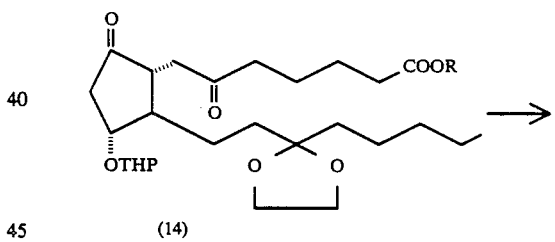
(14)
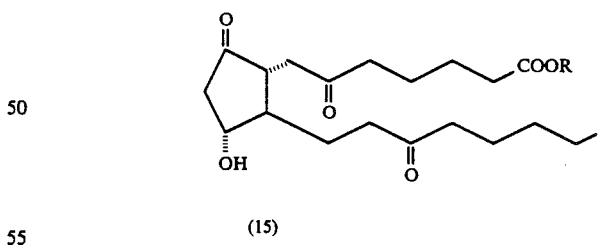
(15)
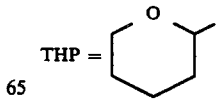
R = lower alkyl Synthetic Chart II
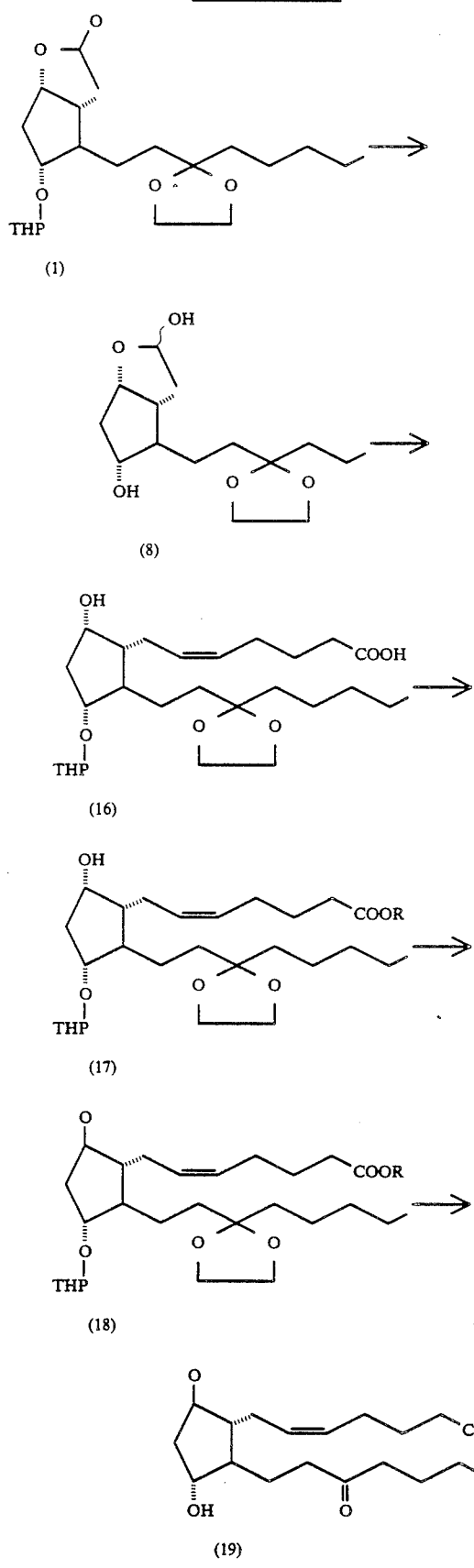
Synthetic Chart III
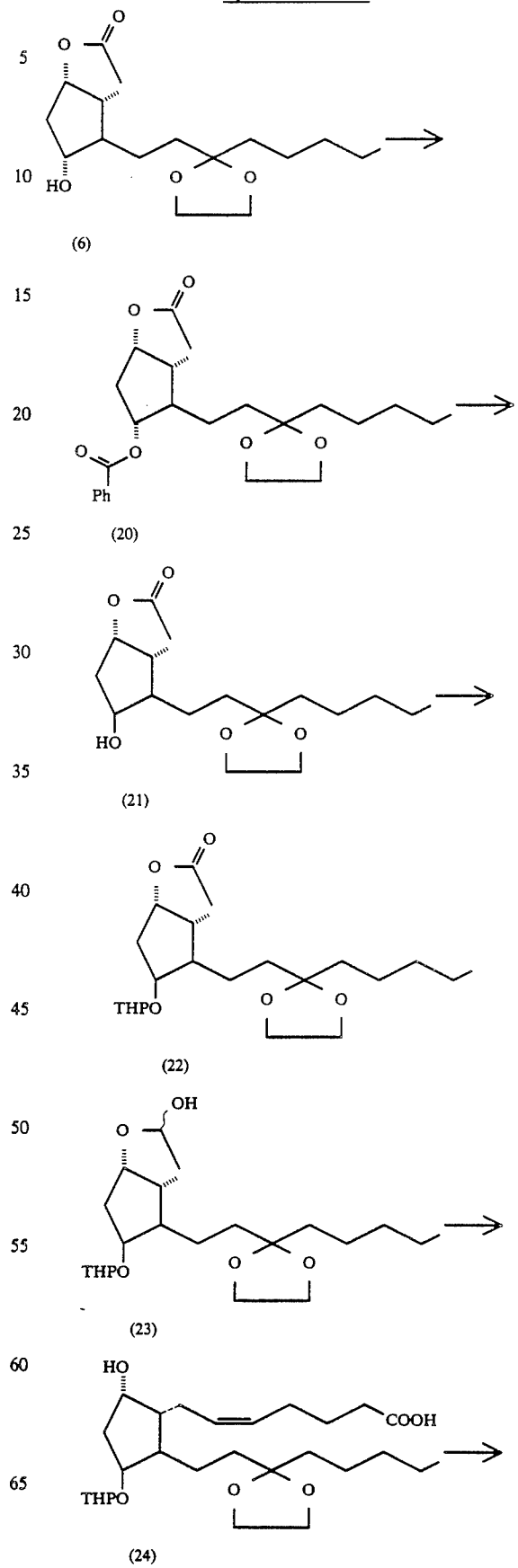

-continued
Synthetic Chart III
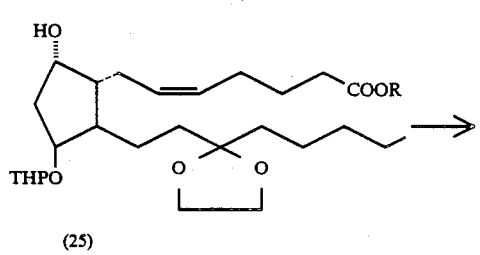
(25)
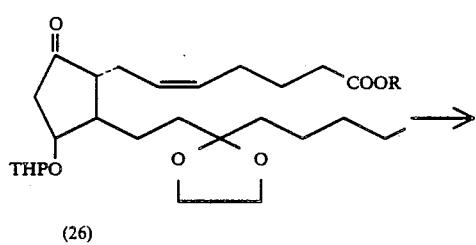
(26)
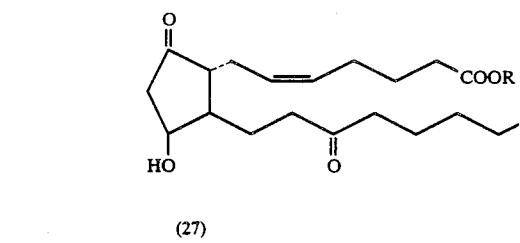
(27)
Synthetic Chart IV
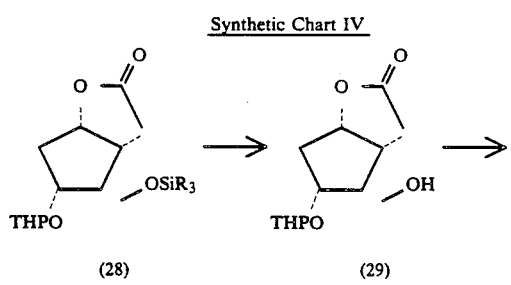
(28)     (29)
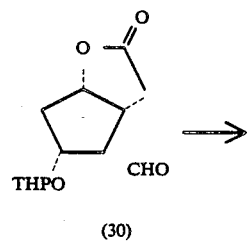
(30)
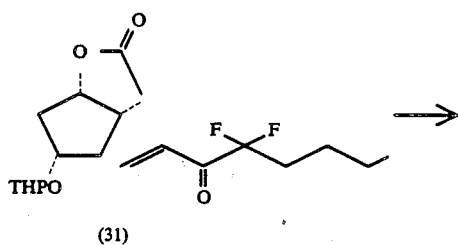
(31)
-continued
Synthetic Chart IV
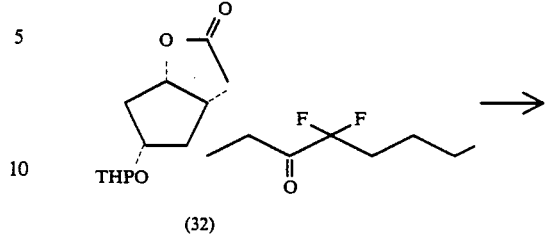
(32)
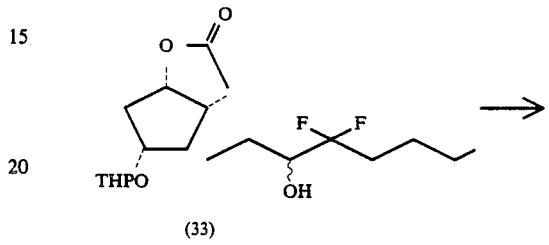
(33)
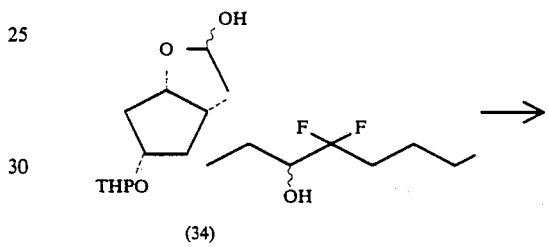
(34)
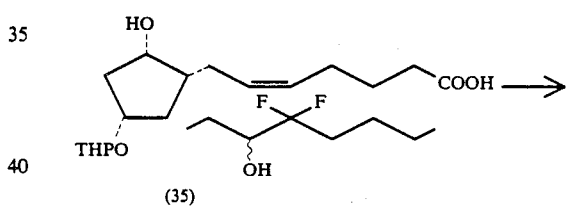
(35)
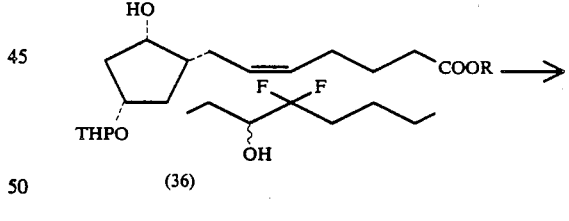
(36)
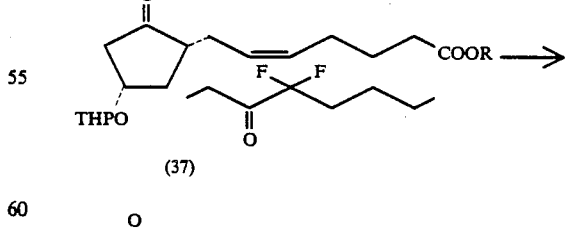
(37)
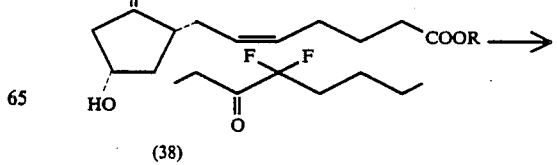
(38)

-continued
Synthetic Chart IV

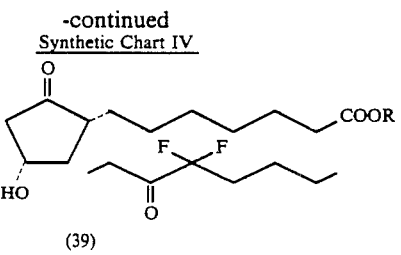

(39)

Since the compounds used in the present invention have a beneficial activity on hepatocytes or biliary cells, these can be used for preparing a medicament. Such activities can be measured by the standard methods.

The compounds used in the present invention may be used as a medicine for animals and human beings and usually applied systemically or locally by such methods as oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As a solid composition of this invention for oral administration, tablets, troches, buccals, capsules, pills, powders, granules and the like are included. The solid composition containing one or more active substances is mixed with at least an inactive diluent, e.g. lactose, mannitol, glucose, hydrocypropyl cellulose, fine crystalline cellulose, starch, polyvinyl pyrolidone, magnesium aluminate metasilicate. The composition may contain additives other than the inactive diluent, for example, lubricants e.g., magnesium stearate, a disintegrator e.g. cellulose calcium gluconates, stabilizers e.g. α-, β- or γ-cyclodextrins, etherated cyclodextrins (e.g. dimethyl-α-, dimethyl-β-, trimethyl-β-, or hyiroxypropyl-β-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may increase the stability of the compounds by forming an inclusion compounds. The stability may be often increased by forming lyposome with phospholipids. Tablets and pills may be coated with an enteric or gastroenteric film e.g. white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed e.g. gelatin. The composition may be in the form of buccals, when an immediate effect is desired. For this purpose, base e.g. glycerine, lactose may be used.

Liquid compositions for oral administration include pharmaceutically acceptable emulsions, solutions, suspensions, syrups, elixirs and the like and contain a generally used inactive diluent e.g. purified water or ethyl alcohol. The composition may contain additives e.g. wetting agents, suspending agents, sweeteners, flavors, perfumes and preservatives.

The composition of the present invention may be sprays which may contain one or more active ingredients and which can be prepared according to a well known methods.

An injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils e.g. olive oil, alcohols, e.g. ethanol and polysorbates. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base e.g. cacao butter and optionally containing nonionic surfactant for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of methyl 16,16-difluoro-13,14-dihydro-15-keto-PGE$_1$ (39)

1-1) Preparation of (1S,5R,6R,7R)-6-hydroxymethyl-7-tetrahydropyranyloxy-2-oxabicyclo[3.3.0]octan-3-one (29)

To a solution of commercial Corey lactone (THP-form, 37.9 g) in tetrahydrofuran was added a solution (1.0 M, 300 ml) of tetrabutylammonium fluoride in tetrahydrofuran and resulting mixture was stirred at room temperature for 3 hours.

Then the reaction mixture was concentrated under reduced pressure and the residue was subjected to column 7 chromatography to give the title compound (29). Yield: 21.70 g (82.8%).

1-2) Preparation of (1S,5R,6R,7R)-6-{(E)-4,4-difluoro-5-oxo-2-octenyl}-7-tetrahydropyranyloxy-2-oxabicyclo-[3.3.0]octan-3-one (31)

A solution (2.0 M, 45.5 ml) of oxalyl chloride in methylene chloride was diluted with methylene chloride under an argon atmosphere at −78° C. To this solution was added dropwise dimethylsulfoxide (12.9 ml) and the resulting mixture was stirred for 10 minutes. A solution (1S,5R,6R,7R)-6-hydroxymethyl-7-tetrahydropyranyloxy-2-oxabicylo[3.3.0]octan-3-one (29) (11.65 g) in methylene chloride was added dropwise and the mixture was stirred for 30 minutes. Then triethylamine (56 ml) was added dropwise and stirring was continued for further 1 hour. The reaction mixture was treated in the conventional manner to give the aldehyde (40) as a crude product.

To a solution of thallium ethoxide (3.26 ml) in methylene chloride was added under an argon atmosphere dimethyl 3,3-difluoro-2-oxoheptylphosphonate (11.9 g) and the resulting mixture was stirred for 1 hour. After cooling the solution to 0° C., a solution of the aldehyde (40) obtained above in methylene chloride was added dropwise to said solution and the mixture was stirred at room temperature for 14 hours. The reaction mixture was treated with acetic acid, celite and a saturated aqueous potassium iodide solution and filtered. The filtrate was treated in the conventional manner and the crude product was subjected to column chromatography to give the tile compound (41).

Yield: 7.787 g (44.3%).

1-3) Preparation or (IS,5R,6R,7R)-6-(4,4-difluoro-5-oxo-octyl)-7-tetrahydropyranyloxy-2-oxabicyclo[3.3.0]octan-3-one (42)

To a solution of (1S,5R,6R,7R)-6-{(E)-4,4-difluoro-5-oxo-2-octenyl}-7-tetrahydropyranyloxy-2-oxabicyclo[3.3.0]octan-3-one (41) (5.57 g) in ethyl acetate was added 5% Pd/C (catalytic amount) and the resulting mixture was shaken under a hydrogen atmosphere at room temperature for 7 hours. The reaction mixture was filtered and the filtrate was concentrated under reduced pressure to give the tile compound (42) as a crude product. Yield: 5.48 g (97.8%).

1-4) Preparation of (1S,5R,6R,7R)-6-(4,4-difluoro-5(RS)-hydroxyoctyl}-7-tetrahydropyranyloxy-2-oxabicyclo[3.3.0]-octan-3-one (43)

To a solution of (1S,5R,6R,7R)-6-(4,4-difluoro-5-oxooctyl)-7-tetrahydropyranyloxy-2-oxabicyclo[3.3.0]octan-3-one (42) (5.48 g) in methanol was added sodium borohydride (0.800 g) at 0° C. and the resulting mixture was stirred for 10 minutes. The reaction mixture was treated in the conventional manner and the obtained crude product was subjected to column chromatography to give the title compound (43). Yield: 5.46 g (99.5%).

1-5) Preparation of 16,16-difluoro-13,14-dihydro-11-tetrahydropyranyloxy-PGF$_{2\alpha}$ methyl ester (46)

A solution of (1S,5R,6R,7R)-6-{4,4-dihydro-5(RS)-hydroxyoctyl}-7-tetrahydropyranyloxy-2-oxabicyclo[3.3.0]-octan-3-one (43) (2.579 g) in toluene was cooled to $-78°$ C. under an argon atmosphere. To this solution was added dropwise a solution (1.5 M, 9.6 ml) of diisobutylalmium hydride in toluene and stirred for 30 minutes. The reaction mixture was treated with methanol and a saturated aqueous Rochelle salt solution. Then the solution was treated in the conventional manner to give the lactol (44) as a crude product.

To a suspension of 4-carboxybutyl triphenyl phosphine bromide (11.72 g) in tetrahydrofuran was added dropwise under an argon atmosphere a solution (1.0 M, 52.84 ml) of potassium tert-butoxide in tetrahydrofuran and the resulting mixture was stirred for 20 minutes. The solution was cooled to 0° C. and combined with a solution of lactol (44) in tetrahydrofuran. The resulting mixture was stirred at room temperature for 15 hours and then treated in the conventional manner to give the carboxylic acid (45) as a crude product.

To a solution of the carboxylic acid (45) in acetonitrile was added under an argon atmosphere 1,8-diazabicyclo[5.4.0]undec-7-ene (DBU) (4.0 ml) and methyl iodide (1.7 ml) and the resulting solution was stirred at 60° C. for 30 hours. The solution was treated in the conventional manner and the product was subjected to column chromatography to give the title compound (46)

Yield: 2.737 g (84.5%).

1-6) Preparation of 16,16-difluoro-13,14-dihydro-15-keto-11-tetrahydropyranyloxy-PGE$_2$ methyl ester (47)

To a solution of Collins reagent, prepared from cromic anhydride (16.18 g) and pyridine (26.2 ml) in the conventional process, in methylene chloride was added a solution of 16,16-difluoro-13,14-dihydro-11-tetrahydropyranyloxy-PGF$_{2\alpha}$ methyl ester (46) (2.646 g) in methylene chloride under an argon atmosphere at $-20°$ C. The resulting mixture was stirred at the same temperature for 2 hours and at $-5°$ C. for 9 hours. The solution was treated and sodium hydrogen sulfate and filtered. The filtrate was concentrated under reduced pressure and the residue was subjected to column chromatography to give the title compound (47).

Yield: 1.890 g (64.4%).

1-7) Preparation of 16,16-difluoro-13,14-dihydro-15-keto-PGE$_2$ methyl ester (48)

Into a mixed solvent of acetic acid : water : tetrahydrofuran (3:1:1) was dissolved 16,16-difluoro-13,14-dihydro-15-keto-11-tetrahydroxypyranyloxy-PGE$_2$ methyl ester (47) (2.809 g) and the resulting solution was stirred at 60° C. for 5 hours. The reaction mixture was concentrated under reduced pressure and the residue was subjected to chromatography to give the title compound (48).

Yield: 1.755 g (75.5%).

1-8) Preparation of 16,16-difluoro-13,14-dihydro-15-keto-PGE$_1$ methyl ester (49)

To a solution of 16,16-difluoro-13,14-dihydro-15-keto-PGE$_2$ methyl ester (48) (1.755 g) in ethyl acetate was added Pd/C (catalytic amount) and the mixture was shaken under a hydrogen atmosphere at room temperature for 6 hours. The reaction mixture was filtered. The filtrate was concentrated and the residue was subjected to column chromatography to give the title compound (49).

Yield: 1.655 g (93.8%).

$^1$H NMR(CDCl$_3$)δ0.87(3H,t,J=7Hz), 1.15–2.05(23H,m), 2.11–2.30(3H,m), 2.50(1H,dd,J=7.5 and 17Hz), 3.10–3.20 (1H,br), 3.71(3H's), 4.05–4.20(1H,m) MS(DI-EI) m/z 404(M+), 355 (M+—H$_2$O—CH$_3$O), 297(M+—C$_5$H$_9$F

FORMULATION EXAMPLE 1

Powders for injection

|  | (Parts by weight) |
|---|---|
| 13,14-dihydro-15-keto-16,16-difluoro-PGE$_2$ | 1 |
| mannitol | 5 |
| distilled water | 0.4 |

The above ingredients were mixed, stirred, sterilized, filtered and lyophilized to give powders for injection.

FORMULATION EXAMPLE 2

Injectable solution

|  | (Parts by weight) |
|---|---|
| 13,14-dihydro-15-keto-16,16-difluoro-PGE$_1$ | 0.2 |
| nonion surfactant | 2 |
| distilled water | 98 |

The above ingredients were mixed and sterilized to give and injectable solution.

FORMULATION EXAMPLE 3

3,14-dihydro-15-keto-16,16-difluoro-20-methyl-PGE$_2$ (50 mg) dissolved in methanol (10ml) was mixed with mannitol (18.5 g). The mixture was screened (with a sieve, the pore size of which being 30 mm in diameter), dried at 30° C. for 90 minutes and screened again. The powders thus obtained were mixed with fine-grain silica gel (Aerosil TM 200 g) and filled in No.3 hard gelatin capsules (100) to give enteric capsules which contain 0.5 mg of 13,14-dihydro-15-keto-16,16-difluoro-20-methyl-PGE$_2$ per capsule.

FORMULATION EXAMPLE 4

Powders for oral administration

|  | (Parts by weight) |
|---|---|
| 13,14-dihydro-6,15-keto-16,16-difluoro-PGE$_1$ methyl ester | 5 |
| light anhydrous silicic acid | 5 |
| Abicel TM | 20 |
| lactose | 70 |

The above ingredients were mixed to give powders for oral administration.

FORMULATION EXAMPLE 5

Soft gelatine capsules

|  | (Parts by weight) |
|---|---|
| 13,14-dihydro-6,15-diketo-19-methyl-PGE$_1$ methyl ester | 1 |
| light anhydrous silicic acid | 899 |
| Panasate TM | 20 |

The above ingredients were mixed and filled in soft gelatine capsules.

FORMULATION EXAMPLE 6

Enteric capsules 16-desbutyl-13,14-dihydro-15-keto-16-m-trifluoromethylphenoxy-PGF$_{2\alpha}$ methyl ester (50 mg) dissolved in methanol (10ml) was mixed with mannitol (18.5 g). The mixture was screened (with a sieve, the pore size of which being 30 mm in diameter), dried at 30° C. for 90 minutes and screened again. The powders thus obtained were mixed with fine-grain silica gel (Aerosil TM, 200 g) and filled in No.3 hard gelatin capsules (100) to give enteric capsules which contain 0.5 mg of 13,14-dihydro-15-keto-16-desbutyl-16-m-trifluoromethylphenoxy-PGF$_{2\alpha}$ methyl ester per capsule.

In the above formulation examples, the active ingredient can be replaced by any other compound within the compounds used in the invention.

TEST EXAMPLE 1

Crj: Wistar male rats (weighing 200–220 g, 7 weeks old) which had been fasting for 16 hours orally received 3 ml/kg of carbon tetrachloride (CCl$_4$) in order to elicit acute hepatopathy. After 24 hours, blood samples were collected under ether anesthesia and sera separated therefrom were assayed for biochemical profile by an automatic analyser (AU 550, Olympus Optics Co. Ltd.). In addition, condition of liver was evaluated by its appearance on the basis of the following scores:
0: no significant change
1: shape unchanged with reddish brown color enlarged with blunted edge, thin red color and clear surface structure
3: further enlarging with deeper brown color The test compound was dissolved in 0.5% ethanoic physiological saline and subcutaneously administered on the dorsa of animals before 24 hours, 0.5 hour and after 6 hours of the oral administration of CCl$_4$. As the test compound, 13,14-dihydro-15-keto-16,16-difluoro-PGE$_2$ was used.

Grouping of animals was as follows:

| Group | Drug | Dose | CCl$_4$ | number |
|---|---|---|---|---|
| 1 | Phys. Sal. | 5 ml/kg | 0 | 5 |
| 2 | 0.5% EtOH Phys. Sal. | 5 ml/kg | 3 ml/kg | 5 |
| 3 | Test Compound | 0.01 mg/kg | 3 ml/kg | 5 |
| 4 | Test Compound | 0.1 mg/kg | 3 ml/kg | 5 |
| 5 | Test Compound | 1.0 mg/kg | 3 ml/kg | 5 |

Phys. Sal.: Physiological Saline

Results

The results of the biochemical tests of blood are shown in Table 1 wherein GPT is glutamic pyruvic transaminase, GOT is glutamic oxaloacetic transaminase, LDT is lactate dehydrogenase and $\gamma$-GTP is gamm glutamyl transpeptidase. The values are shown in mean ±SD (standard deviation).

The weight of liver, liver/body weight ratio and macroscopic anatomical observation (shown in scores) are shown in Table 2.

TABLE 1

| Group | GPT (IU/l) | GOT (IU/l) | NH$_3$ (mg/dl) | LDH (IU/l) | $\gamma$-GTP (IU/l) |
|---|---|---|---|---|---|
| 1 | 36 ± 6 | 100 ± 25 | 123 ± 39 | 540 ± 314 | 0.6 ± 0.2 |
| 2 | 2918 ± 1416 | 16590 ± 2227 | 1110 ± 364 | 86906 ± 23158 | 4.3 ± 1.1 |
| 3 | 1736 ± 430 | 8900** ± 2438 | 820 ± 108 | 55152* ± 11740 | 3.8 ± 2.6 |
| 4 | 1670 ± 1026 | 8483** ± 4119 | 613 ± 152 | 39358** ± 18709 | 3.3 ± 0.6 |
| 5 | 1240* ± 652 | 9582** ± 3245 | 566* ± 72 | 33282** ± 13528 | 3.5* ± 4.4 |

TABLE 2

| Group | weight of liver (g) | liver/body weight ratio (%) | score |
|---|---|---|---|
| 1 | 11.23 | 4.78 | 0 |
| 2 | 11.25 | 5.79 | 2.8 |
| 3 | 11.51 | 5.87 | 2.8 |
| 4 | 10.56 | 5.64 | 2.5 |
| 5 | 10.16* | 4.95* | 1.2* |

Dunnet test, *P < 0.05, **p < 0.01

Postnecrotic degeneration of liver was reduced in Group 5 as compared with Group 2 judging from macroscopic anatomical observation (score). Also, the same tendency was observed in Group 4, though is was not significant.

Increase in liver weight by carbon tetrachloride was reduced but insignificantly in Groups 4 and 5. The reduction of increase in liver/body weight ratio was significant in Group 5.

Among the biochemical test, increases in GPT, GOT, LDH, $\gamma$-GTP and NH$_3$ by administration of carbon tetrachloride were significantly reduced in Group 5 and reduction of increase in GOT and LDH were commonly observed in Groups 3, 4 and 5.

It can be concluded from the above results that the compound used in the present invention is effective in relieving experimental acute hepatopathy.

TEST EXAMPLE 2

Method

The procedure of Test Example 1 was repeated except that 13,14-dihydro-15-keto-16R,S-fluoro-$PGE_2$ was used as the test compound.

Grouping of animals was the same as that in Test Example 1.

Results

The results of biochemical test and macroscopic anatomical observation (score) are shown in Table 3.

TABLE 3

| Group | GPT (IU/l) | GOT (IU/l) | $NH_3$ (mg/dl) | LDH (IU/l) | γ-GTP (IU/l) | score |
|---|---|---|---|---|---|---|
| 1 | 33 ± 5 | 95 ± 23 | 130 ± 55 | 901 ± 299 | 0.84 ± 0.17 | 0 |
| 2 | 2720 ± 1920 | 13598 ± 2558 | 1040 ± 324 | 61560 ± 22742 | 2.98 ± 1.28 | 2.6 |
| 3 | 3403 ± 2393 | 16373 ± 3776 | 1045 ± 524 | 76310 ± 29440 | 2.10 ± 1.17 | 2.8 |
| 4 | 2200 ± 460 | 15445 ± 1268 | 870 ± 323 | 76438 ± 12683 | 2.65 ± 0.69 | 2.0 |
| 5 | 2006 ± 1415 | 11860 ± 5149 | 720 ± 303 | 37290 ± 21956 | 1.24 ± 0.63 | 1.2* |

Dunnet test, *p < 0.05

A tendency of relieving is observed in Group 5 in connection with every items, though it was not significant. In Group 4, the same tendency was observed relating to GPT and $NH_3$.

Among the macroscopic anatomical observation, postnecrotic degeneration of liver was reduced in Group 5 was compared with the control group.

It can be said from the above results that the compound used in the present invention is effective in relieving experimental acute hepatopathy.

TEST EXAMPLE 3

Method

The procedure of Test Example 1 was repeated except that 13,14-dihydro-6,15-diketo-19-methyl-$PGE_1$ ethyl ester—dimethylcyclodextrin adduct (13,14-dihydro-6,15-diketo-19-methyl-$PGE_1$ ethyl ester: dimethylcyclodextrin=1:10) was used as the test compound.

Grouping of animal was as follows:

| Group | Drug | Dose | $CCl_4$ | number |
|---|---|---|---|---|
| 1 | Phys. Sal. | 5 ml/kg | 0 | 5 |
| 2 | 0.5% EtOH Phys. Sal. | 5 ml/kg | 3 ml/kg | 5 |
| 3 | DMCD | 50 mg/kg | 3 ml/kg | 5 |
| 4 | Test Compound | 2.2 mg/kg | 3 ml/kg | 5 |
| 5 | Test Compound | 11 mg/kg | 3 ml/kg | 5 |
| 6 | Test Compound | 55 mg/kg | 3 ml/kg | 5 |

Phys. Sal.: Physiological Saline
DMCD: Dimethylcyclodextrin

Results

The results are shown in Table 4.

TABLE 4

| Group | GPT (IU/l) | GOT (IU/l) | $NH_3$ (mg/dl) | LDH (IU/l) | γ-GTP (IU/l) |
|---|---|---|---|---|---|
| 1 | 37 ± 6 | 93 ± 14 | 119 ± 11 | 806 ± 223 | 0.0 ± 0.00 |
| 2 | 2290 ± 831 | 13194 ± 1856 | 1136 ± 148 | 77154 ± 19839 | 0.46 ± 0.78 |
| 3 | 2002 ± 1119 | 13080 ± 3666 | 758 ± 226 | 61590 ± 14135 | 1.20 ± 1.00 |
| 4 | 2090 ± 752 | 13042 ± 2477 | 1018 ± 257 | 70684 ± 8391 | 0.78 ± 1.22 |
| 5 | 2650 ± 940 | 14078 ± 4033 | 1168 ± 342 | 72556 ± 22571 | 0.54 ± 0.50 |
| 6 | 1942 ± 1041 | 15744 ± 7068 | 614** ± 202 | 76404 ± 39662 | 0.08 ± 0.11 |

Dunnet test, **p < 0.01

In the biochemical test of blood, a tendency of reduction was observed in Group 6 relating to $NH_3$ and GPT.

It can be confirmed from the above results that the compound used in the present invention is effective in relieving experimental acute hepatopathy.

TEXT EXAMPLE 4

Method

The procedure of Test Example 1 was repeated except that the following compounds are used as the test compounds.

1: 13,14-dihydro-15-keto-16,16-difluoro-$PGE_2$ methyl ester
2: 13,14-dihydro-15-keto-16,16-difluoro-20-methyl-$PGE_2$
3: 13,14-dihydro-15-keto-16,16-difluoro-$PGE_1$ methyl ester
4: 13,14-dihydro-15-keto-16R,S-fluoro-$PGE_1$
5: 13,14-dihydro-16,15-diketo-16R,S-fluoro-$PGE_1$ ethyl ester
6: 13,14-dihydro-15-keto-16,16-difluoro-$PGE_{2\alpha}$ methyl ester
7: 13,14-dihydro-15-keto-20-ethyl-$PGE_{2\alpha}$ isopropyl ester
8: 13,14-dihydro-15-keto-16,16-difluoro-$PGE_1$
9: 13,14-dihydro-15-keto-16,16-difluoro-11-dehydroxy-11-methyl-$PGE_2$ methyl ester Grouping of animals was as follows:

| Group | Drug | Dose | $CCl_4$ | number |
|---|---|---|---|---|
| 1 | Phys. Sal. | 5 ml/kg | 0 | 5 |
| 2 | 0.5% EtOH Phys. Sal. | 5 ml/kg | 3 ml/kg | 5 |
| 3 | Test Compound (Table 5) | | 3 ml/kg | 5 |

Phys. Sal.: Physiological Saline

Results

In the biochemical test of blood, the results are shown in Table 5 as reduction in % caused by administration of the test compounds in Group 3 as compared with the increase in weight of liver, which is taken as 100%, due to carbon tetrachloride, in Group 2.

Liver/body weight ratio and macroscopic anatomical observation (score) are shown in Tables 6–10.

TABLE 5

| Test Compound | Dose (mg/kg) | Reduction (%) | | | | |
|---|---|---|---|---|---|---|
| | | GPT | GOT | T-Bil | NH$_3$ | LDH |
| 1 | 1.0 | 58* | 43 | 29 | 29 | 62** |
| 2 | 1.0 | 38 | 30 | 49 | 47 | 48 |
| 3 | 1.0 | 34 | 30 | 39 | 55* | 40 |
| 4 | 3.0 | — | — | 28 | 22 | 24 |
| 5 | 1.0 | 34 | 29 | 13 | 26 | — |
| 6 | 10.0 | 31 | 40 | — | 47* | 55* |
| 7 | 50.0 | 37 | 21 | 66* | 30 | 31 |
| 8 | 1.0 | 47 | 32 | — | — | 47* |
| 9 | 0.1 | — | — | 29 | 26 | 17 |

Dunnet test, *p < 0.05, **p < 0.01

TABLE 6

(Test Compound 1)

| Group | Liver/Body weight ratio (%) | Score |
|---|---|---|
| 1 | 4.85 | 0 |
| 2 | 5.56 | 2.6 |
| 3 | 5.12 | 1.8 |

TABLE 7

(Test Compound 2)

| Group | Liver/Body weight ratio (%) | Score |
|---|---|---|
| 1 | 4.99 | 0 |
| 2 | 6.06 | 3.0 |
| 3 | 5.13 | 2.8 |

TABLE 8

(Test Compound 3)

| Group | Liver/Body weight ratio (%) | Score |
|---|---|---|
| 1 | 4.92 | 0 |
| 2 | 5.73 | 3.0 |
| 3 | 4.88* | 1.4* |

TABLE 9

(Test Compound 7)

| Group | Liver/Body weight ratio (%) | Score |
|---|---|---|
| 1 | 4.81 | 0 |
| 2 | 6.52 | 3.0 |
| 3 | 5.26** | 1.6* |

TABLE 10

(Test Compound 8)

| Group | Liver/Body weight ratio (%) | Score |
|---|---|---|
| 1 | 5.08 | 0 |
| 2 | 6.45 | 3.0 |
| 3 | 5.02** | 2.0 |

Dunnet test, *p < 0.05, **p < 0.01

TEST EXAMPLE 5

Method

Male Wister rates (weighing 200–220 g) were allotted to groups of five animals and fasted for 16 hours. Then carbon tetrachloride (3 ml/kg) was orally administered to animals. After 24 hours, blood samples were collected from animals under ether anesthesia and alkaline phosphatase activity (ALP) in sera were determined. The test compounds, listed below, were dissolved in a physiological saline and subcutaneously administered on the dorsa of the animal before 24 hours, 0.5 hour and after 6 hours of the administration of carbon tetrachloride. The control group received the physiological saline.

Test Compound

1: 13,14-dihydro-15-keto-16,16-difluoro-PGE$_2$
2: 13,14-dihydro-15-keto-16,16-difluoro-PGE$_2$ methyl ester
3: 13,14-dihydro-15-keto-16,16-difluoro-20-methyl-PGE$_2$
4: 13,14-dihydro-6,15-keto-16R,S-fluoro-PGE$_2$ ethyl ester
5: 13,14-dihydro-15-keto-16,16-difluoro-PGF$_{2\alpha}$ methyl ester
6: 13,14-dihydro-15-keto-16,16-difluoro-PGE$_1$ methyl ester
7: 13,14-dihydro-15-keto-20-ethyl-PGF$_{2\alpha}$ isopropyl ester
8: 13,14-dihydro-15-keto-16,16-difluoro-11-dehydroxy-11-methyl PGE$_2$ methyl ester Results The results are shown in Table 11 as reduction in % caused by administration of the test compounds as compared with the increase in alkaline phosphatase activity which is taken as 100%.

TABLE 11

| Test Compound | Dose (mg/kg) | Reduction in Increase of ALP (%) |
|---|---|---|
| 1 | 1 | 75 |
| 2 | 1 | 20 |
| 3 | 1 | 34 |
| 4 | 5 | 13 |
| 5 | 10 | 25 |
| 6 | 1 | 85* |
| 7 | 50 | 75* |
| 8 | 0.1 | 14 |

Dunnet test, *p < 0.05

It can be concluded from the above results that the compounds used in the present invention are useful as treating agents for hepatobiliary diseases because of their activity of reducing increase of alkaline phosphatase activity which is an indicative enzyme for hepatobiliary disease.

TEST EXAMPLE 6

Five male Crj: Wister rats (7 weeks old, weighing 200–220 g) per group were used in the test For subcutaneous administration, the test compound was dissolved in 0.5% ethanolic physiological saline so as to be administered in a dose of 5 ml/kg body weight.

The rats were fasted for 18 hours. Then they received orally 60% ethanol (12 ml/kg). The test compounds were subcutaneously administered on the dorsa of the animals before 0.5 hour, after 2 hours and 8 hours of the administration of ethanol. After 24 hours, the liver was removed from each of the animals under ether anesthesia and weighed. As the test compound, 13,14-dihydro-15-keto-16,16-difluoro-PGE$_2$ was used.

Grouping of animals was as follows:

| Group | Drug | Dose | 60% EtOH |
|---|---|---|---|
| 1 | Phys. Sal. | 5 ml/kg | 0 |
| 2 | 0.5% EtOH Phys. Sal. | 5 ml/kg | 12 ml/kg |
| 3 | Test Compound | 1 μg/kg | 12 ml/kg |
| 4 | Test Compound | 10 μg/kg | 12 ml/kg |

Phys. Sal.: Physiological Saline

Results

The results are shown in Table 12.

TABLE 12

| Group | Weight (g) | Liver/Body weight ratio (%) |
|---|---|---|
| 1 | 5.79 ± 0.26 | 3.16 ± 0.94 |
| 2 | 7.24 ± 0.40 | 3.92 ± 0.28 |
| 3 | 7.06 ± 0.21 | 3.88 ± 0.07 |
| 4 | 6.63 ± 0.03* | 3.67 ± 0.10* |

(Values are shown in Mean ± Standard Deviation.)

A tendency of reducing increase in liver weight as compared with Group 2 was observed in Group 3, though it is not significant and the deduction was significant in Group 4.

It can be seen from the above results that the compounds of the present invention are effective in relieving experimental acute hepatopathy caused by ethanol.

What we claim is:

1. A method for treatment of a hepatopathy or a biliary tract disorder which comprises administering, to a subject in need of such treatment, a 15-ketoprostaglandin compound in an amount effective in treatment of the hapatopathy or biliary tract disorder.

2. The method according to claim 1, in which the hapatopathy is an acute hepatopathy.

3. The method according to claim 1, in which said 15-ketoprostaglandin compound is a 16-mono- or di-halo-15-ketoprostaglandin compound.

4. The method according to claim 1, in which said 15-ketoprostaglandin compound is a 13,14-dihydro-16-mono- or di-halo-15-ketoprostaglandin compound.

5. The method according to claim 1, in which said 15-ketoprostaglandin compound is a 13,14-dihydro-16-mono- or di-fluoro-15-ketoprostaglandin compound.

6. The method according to claim 1, in which said 15-ketoprostaglandin compound is a 6,15-diketoprostaglandin compound.

7. The method according to claim 1, in which said 15-ketoprostaglandin compound is a 13,14-dihydro-6,15-diketo-prostaglandin compound.

8. The method according to claim 1, in which said 15-ketoprostaglandin compound is a 15-keto-19-alkyl-prostaglandin compound.

9. The method according to claim 1, in which said 15-ketoprostaglandin compound is a 13,14-dihydro-15-keto-19-alkyl-prostaglandin compound.

10. A method for treatment of a hepatopathy which comprises administering, to a subject in need of such treatment, a 15-ketoprostaglandin E compound in an amount effective in treatment of a hepatopathy.

11. The method according to claim 10, in which said 15-ketoprostaglandin E compound is a 16-mono- or di-halo-15-ketoprostaglandin E compound.

12. The method according to claim 10, in which said 15-ketoprostaglandin compound is a 13,14-dihydro-16-mono- or di-halo-15-ketoprostaglandin E compound.

13. The method according to claim 10, in which said 15-ketoprostaglandin compound is a 13,14-dihydro-16-mono- or di-fluoro-15-ketoprostaglandin E compound.

14. The method according to claim 7, in which said 15-ketoprostaglandin compound is a 6,15-diketo-prostaglandin E compound.

15. The method according to claim 1, in which the treatment is for fulminant hepatitis, fatty liver, hepatic coma, acute or chronic hepatitis, heptatolenticular degeneration, heptic hyperthropy, portal hypertension, obstructive jaundice, liver abscess, cirrhosis, parasitic hepatopathy, hepatophyma, liver tuberculosis, choloecystisis, cholelithiasis, cholangitis, biliary colic, or fat hypersensitivity.

* * * * *